United States Patent [19]

Li et al.

[11] Patent Number: 5,527,671
[45] Date of Patent: Jun. 18, 1996

[54] ASSAY FOR *VERTICILLIUM DAHLIAE*

[75] Inventors: Kening Li; Douglas I. Rouse, both of Madison; Thomas L. German, Hollandale, all of Wis.

[73] Assignee: Wisconsin Alumni Research Foundation, Wis.

[21] Appl. No.: 335,565

[22] Filed: Nov. 7, 1994

[51] Int. Cl.$^6$ .............................. C12Q 1/68; C12P 19/34
[52] U.S. Cl. .................................................. 435/6; 435/91.2
[58] Field of Search ........................................ 435/6, 91.2

[56] References Cited

PUBLICATIONS

Atlas et al. (1990) pp. 399–406 in "PCR Protocols" Ed. Innis et al. Academic Press, Inc.
Nazar et al. (1991) Physiol. and Molec. Plant Pathology 39: 1–11.
Young et al. (1993) Appl. and Environ. Microbiol. 59(6): 1972–1974.
Gilliland et al. (1990) pp. 60–69 in "PCR Protocols" Ed. Innis et al. Academic Press, Inc.

*Primary Examiner*—W. Gary Jones
*Assistant Examiner*—Ethan Whisenant
*Attorney, Agent, or Firm*—Quarles & Brady

[57] ABSTRACT

A DNA sequence is described which is diagnostic of *Verticillium dahliae*, a problematic plant pathogen. The sequence is found only in *V. dahliae* and not in closely related Verticillium species. The identification of this diagnostic DNA sequence permits a rapid and sensitive PCR assay to be used to test soil samples for the presence of this pathogen. Competitive PCR may be used to quantify the amount of pathogen present.

7 Claims, 2 Drawing Sheets

```
                        primer VDS1
    1   AACGGTGACC ACATTCAGTT CAGGAGACGG AAGGAGGAAA TCGATCTTGA

51   ATCTCTCGAG ATCGAAGAGT GAACCCAGTT TTAGTGCGGA CTGAGCTCCA

101   GAACTTTTTC TTGCTGGTGA CATTGCACAT GGCCGGACyG TGAAGACCGG
        primer VDSeq1
  151   CCATCTTATC ACCTGAAGCA TAGAGTCGAT ATTAGGTACA ATTTGTTCGC 201   AAAACCGATC CGTGTTCGTG AAGAGACTCG GCCAGAGTGC CTCyCACACT

251   GGAGATAGCC TGTAACACCA CTGCTACACC ATGAAAGCCT TGTGTCATTT

301   CATGTTACCT TACCTGTCAC AAGGTCCAGT GAATGATGTT GCCACGCAAT

351   TACTTGAGTA TAGGGCCCTG GCACATGTAC CCTCRGTGTC RCGGAGGAGA
                           primer VDSeq2
  401   CCTGCAAGTA GACCCTTCTA CCCACGAATC ACACRTACTG TGAGGTTCTG 451   TTTGCCCACC CCTCTATRAA GAAGAGACCT CCCCCCTTGA GAGGGGCTCC
                                         primer VDS2
  501   TCTCTTGCTC CTTCTACTGG AGTATTTCGG TCCATGCATA TGAAATACAT

551   CCACTGAGGT CACCGTT
```

FIG. 1

```
      primer VDS1
   1  ATTCAGTTCA GGAGACGGAG CAAATTTTAT CAGATTCTAC TTGGGCTCCT

51  TCAAGTAAGA TCCATTCATT CGTCCTGATT CGTGGAAGCA TCCCACTCTT

101  CTCCCAGTCA CCCTACTCTT TCAAACCCGT GCCACAGGTT CATCATTCTA

151  CCGAAACAAA TTATGAAGCT TTAAGAAGC ATTTTGATAA TGTAACTGAT

201  CGTTACGGGG CCGTTCAAGT GGCTTCGTTA GTGGAGAAAC ATGGACCTGA

251  GGCAATAGTT GGTGGAGAAT ACGAGAAGTT GTCGACTCTT CTCAATGTGT

301  CCCGAGCTGG CGAAAACAAA AAGCTCCATT GGGTTTGAGT GGTTTGATTT

351  CCATGCTATA TGTAAAGGCA TGAAATTCGA GAACGTCACC TTCTACTGGA
      primer VDS2
 401  GTATTTCGG
```

FIG. 2

ASSAY FOR *VERTICILLIUM DAHLIAE*

STATEMENT REGARDING FEDERALLY-SPONSORED RESEARCH

This invention was made with United States Government support awarded by USDA, Grant #USDA #58-1275-1-135. The United States Government has certain rights in this invention.

FIELD OF THE INVENTION

The present invention relates to diagnostics for plant pathogens and relates, in particular, to a DNA diagnostic for a particular Verticillium species.

BACKGROUND OF THE INVENTION

Certain fungal diseases are significant economic problems with regard to some crop species. One of the class of fungi which are pathogens of many crops belong to the Verticillium genus of fungal pathogens which includes two economically important plant pathogens, *Verticillium dahliae* and *Verticillium albo-atrum*. *Verticillium dahliae* is a particularly problematic pathogen for potato. In current agronomic practices, farmers raising potatoes are forced to soil fumigants to control the presence of *Verticillium dahliae*. Otherwise, farmers run the risk that large portions of their crop will be lost to an early dying disease caused by the fungus. However, *Verticillium dahliae* is not present in all of the fields in which potatoes are grown. Even in infected fields, the level of infection is not always significant. Typically, in current practice, the soil fumigation is applied to the fields in which potato is to be grown whether or not *Verticillium dahliae* is present, just to avoid a catastrophic loss of the crops. The soil fumigation process is, however, quite expensive and is environmentally undesirable. It is therefore desirable to diagnose in advance whether or not *Verticillium dahliae* is present in the fields in which potatoes are to be grown, so as to determine whether or not soil fumigation is necessary in order to safely cultivate potatoes in the field.

Existing protocols for diagnosis of Verticillium species rely on in vitro culture of soil samples using selective media. The selective media are, at least in theory, selective for the presence of the particular species *Verticillium dahliae*. However, existing tests report large numbers of false negative responses. In addition, the tests are laborious and take three to four weeks to perform, which can be an unsatisfactory time period for agricultural purposes. Accordingly, a faster and more accurate diagnostic test for the presence of *Verticillium dahliae* would be useful in commercial potato growing.

One method that is developed as a general assay for biological systems is based on the polymerase chain reaction referred to as PCR. Using PCR, it is possible to make many copies, in a process referred to as amplification, of a desired DNA sequence if, and only if, the sequence is present in an environmental or other specimen. Thus, if a DNA sequence is known which is diagnostic of a particular species or condition, it becomes possible to perform a PCR analysis on an environmental sample, amplifying the specific DNA in question, and thus be able to determine whether or not the organism in question was present in that sample.

The PCR process is keyed by primers, which are specific to a DNA sequence to be amplified. PCR primers have been developed which allow for detection of Verticillium fungi.

However, the previously known differences between *V. dahliae* and *V. albo-atrum* are based on a single, or very few, base pair differences. Thus, a PCR assay based on those few differences requires very stringent conditions to be effective. Prior to the method described here, no known larger DNA sequence was diagnostic of *Verticillium dahliae* and capable of distinguishing it from *V. albo-atrum.*

SUMMARY OF THE INVENTION

The present invention is summarized in that a DNA fragment has been characterized which is characteristic of *Verticillium dahliae* and allows for the rapid and efficient assay of an environmental soil sample to determine whether or not *Verticillium dahliae* is present in the particular sample.

The present invention is also directed to primers which may be used in a PCR analysis to test an environmental sample to determine whether or not the sample contains *Verticillium dahliae.*

It is an advantage of the present invention in that it enables an efficient, quick, and cost-effective assay of an environmental sample to determine whether or not the sample contains *Verticillium dahliae.*

It is a feature of the present invention in that the rapid and efficient assay for the presence of *Verticillium dahliae* permit soil samples to be tested in a timely fashion at the initiation of the growing season to avoid unnecessary application of fumigants to the soil in areas which do not have the fungal pathogen present.

Other objects, advantages, and features of the present specification will become apparent from the following specification.

BRIEF DESCRIPTION OF THE DRAWINGS

FIG. 1 is a sequence listing of the DNA sequence diagnostic for *V. dahliae.*

FIG. 2 is a sequence listing of the internal standard for competitive PCR analysis.

DESCRIPTION OF THE INVENTION

The present invention is premised on the fact that a DNA sequence has been identified which has a specific marker for fungal pathogens of the species *Verticillium dahliae* and is not found in other plant pathogens tested. Using the tools of modern molecular biology, it is therefore possible to use a variety of techniques to test for the presence, or absence, of that particular DNA fraction in a pathogen of uncertain or unknown taxonomy, to determine if it is, or is not, a *Verticillium dahliae* isolate. The preferred method for performing such an assay is based on the polymerase chain reaction (PCR) which allows for rapid and efficient amplification of the DNA sequence in a sample of unknown origin, but other methods for detection of this DNA fragment are possible. It is also possible, using techniques such as competitive PCR, to semi-quantitate the amount of *Verticillium dahliae* present in a given environmental sample so as to determine not only absolutely whether or not the pathogen is present, but also something about the level at which it is found in that particular environment.

The nucleotide sequence which is found to be diagnostic for *Verticillium dahliae* is a 567 base pair sequence set forth in SEQ ID NO 1 below. The sequence was discovered, as described in greater detail below, by a methodology based on random amplified polymorphic DNA (RAPD). In short, RAPD primers were used to randomly amplify DNA generated from a variety of plant pathogenic fungi and then the amplified fragment were screened for fragments unique to the *Verticillium dahliae* species. The fragment has proved to be diagnostic of *Verticillium dahliae* in that PCR tests have shown that primers specific to this fragment amplify DNAs from all tested *V. dahliae* isolates from diverse hosts and geographic origins but the same primers fail to amplify DNA from any other sources tested, including closely related fungal pathogenic species such as *V. albo-atrum*.

If qualitative analysis, without quantitative analysis, is all that is required to test for the presence or absence of *V. dahliae* in a particular environmental sample, any of a wide variety of DNA analytical techniques may be used in place of the PCR assay. It is possible to construct DNA to DNA or RNA to DNA hybridization probes to test for the presence of absence of target DNA in a sample. There are also other nucleotide amplification techniques that can be used to amplify the DNA, or its transcript, which is diagnostic of *V. dahliae*.

Quantification of microorganisms in the environment is another often challenging problem in microbiology. It has been found here that competitive PCR may be used to quantify the amount of DNA from *V. dahliae* which is found in a particular environmental sample. Competitive PCR is currently considered the state of the art method to quantify specific nuclear acid sequences in a given sample. In competitive PCR, a known number of copies of an internal standard is introduced into the same PCR reaction as is conducted with the environmental sample. Since the internal standard and the target DNA, presumably present in some level in the sample, differ slightly in size, enough to allow easy differentiation on gel electrophoresis, but not so long as to effect the efficiency of the polymerase chain elongation step, the target and the standard compete for the same set of primers. Thus, the other numerous and uncharacterizable, and sometimes unknown, variables effecting the yield of PCR products are circumvented by simply making a comparative analysis between the quantification of the target DNA and the quantification of the standard, since the original number of known copies of the standard is controlled. The amount of microorganism can then be inferred from the amount of nucleic acid of the target which has been found in the sample.

Thus the internal standard to be used for competitive PCR is constructed in such a way that it is amplified with the same pair of primers as the target sequence, yet is readily distinguishable from the sequence by size. In order to generate the competitive PCR internal standard, the applicants here performed non-specific PCR in a number of unrelated DNAs from unrelated organisms. From the amplification profile, a band originated from *Sclerotinia sclerotiorum* was selected that differed slightly in size from the target fragment *V. dahliae*. This band was purified, cloned, and sequenced. The sequence had two regions at each of its ends which corresponded to the specific PCR primers to be used with the *V. dahliae* fragment, but was otherwise entirely unrelated to the sequence from *V. dahliae*. This fragment was then selected as the internal standard to be used within the method of the present invention, and the sequence is set forth in SEQ ID NO 2 below.

It is to be understood that the fungal pathogens of the species *Verticillium dahliae* are only one of a number of pathogenic species within the genus. There is a very closely related fungal pathogen, *Verticillium albo-atrum* which is difficult to distinguish from *V. dahliae* in many diagnostic tests. Using currently available PCR primers which are intended to be specific for *V. dahliae*, the difference is based on a single or very small number of nucleotide differences between *V. dahliae* and *V. albo-atrum*. This small amount of differences thus require strict and stringent PCR conditions for successful differentiation of samples of the two materials. In view of the fact that the samples sought to be assayed here are from the soil, contamination and strict handling of environmental samples would be problematic. The technique of the present invention does not require the same degree of stringent handling of the material, since the diagnostic sequence set forth in SEQ ID NO 1 below does not appear in *V. albo-atrum*. Accordingly, the test is much more diagnostic and effective.

In accordance with the present invention, it is intended that soil samples can be tested for the presence or absence of DNA indicative of *Verticillium dahliae* by performing a PCR analysis on the soil samples or extracts from the soil samples. Quantitative data can be generated by competitive PCR using the internal standard described herein. Based on this information, an estimate can be made as to the quantitative level of *V. dahliae* in any particular farm field. The grower, with or without consultants, can then determine based on the level of *V. dahliae* found in the particular field whether or not it is cost justified and agronomically necessary to apply soil fumigants to the fields in question. In areas where *V. dahliae* is scarce, the environmentally questionable practice of soil fumigation can be avoided and many can be saved.

In performing a PCR analysis, the selection of the particular probes is subject to much variation. Shown in FIG. 1 is the sequence of the 567 base pair *V. dahliae* sequence. The binding site for the PCR primers, here designated VDS1 and VDS2, are shown in the sequence. Any primers which bind to these primers can be used in the present method. The preferred primers VDS1 and VDS2 are presented as SEQ ID NO 32 and SEQ ID NO 33 below. The corresponding primer binding sites on the internal standard are also shown in FIG. 2.

In performing the sequencing of the 567 base pair diagnostic sequence for *V. dahliae*, two other useful primers were developed, designated VDSeq 1 and VDSeq 2. Those primers are indicated in FIG. 1. These primers were found to have the same level of specificity as VDS1 and VDS2, further confirming the unique character of the diagnostic sequence. The primers VDSeq 1 and VDSeq 2 can be used to PCR amplify the diagnostic 567 base pair sequence or can also be used to verify that the PDR product of VDS1 and VDS2 is the desired fragment.

EXAMPLES

The origins and identities of the source fungal isolates which were used in the study described below are shown in Table 1 below. The Verticillium isolates used were derived from single conidial spores produced on potato dextrose agar. All single-spore cultures were examined microscopically to confirm their identities.

TABLE 1

Designation of identities, Geographic origins,
Host Origins and Sources of Fungal Isolates

| Isolate Designation | Identification | Geographical Origins[1] | Host Origins[1] | Source[2] |
|---|---|---|---|---|
| V18 | V. dahliae | | | D. I. Rouse |
| V14 | V. dahliae | Wisconsin | Potato | D. I. Rouse |
| V1654 | V. sp.[3] | Wisconsin | Poppy | D. I. Rouse |
| V1665 | V. dahliae | Wisconsin | Potato | D. I. Rouse |
| LV63 | V. dahliae | Wisconsin | Potato | K.-N. Li |
| LV64 | V. dahliae | Wisconsin | Potato | K.-N. Li |
| LV75 | V. dahliae | Oregon | | D. I. Rouse |
| Mint(UMD-7) | V. dahliae | Michigan | Peppermint | D. I. Rouse |
| B111 | V. dahliae | Syria | Cotton | A. Bell |
| B112 | V. dahliae | Syria | Cotton | A. Bell |
| B207 | V. dahliae | Australia | Cotton | A. Bell |
| ARW | V. dahliae | USSR | Aslespas sp. | A. Bell |
| CRC | V. dahliae | USSR | Cotton | A. Bell |
| DV5RI | V. dahliae | Rhode Island | Potato | J. Davis |
| PR | V. dahliae | USSR | Peach | A. Bell |
| RU | V. dahliae | USSR | Cotton | A. Bell |
| RP | V. dahliae | USSR | Potato | A. Bell |
| RGG | V. dahliae | N. Carolina | Tomato | R. Rowe |
| MT | V. dahliae | Canada | Maple | A. Bell |
| HO-1 | V. dahliae | Oregon | Hops | A. Bell |
| 277 | V. dahliae | Washington | Sugarbeet | A. Bell |
| PW | V. dahliae | Wisconsin | Potato | A. Bell |
| TA | V. dahliae | Idaho | Potato | A. Bell |
| SZ-1(=CS-1) | V. dahliae | Swaziland | Cotton | A. Bell |
| CW (49) | V. dahliae | Washington | Cherry | A. Bell |
| FN (37) | V. dahliae | Australia | Flax | A. Bell |
| MC (79) | V. dahliae | California | Chrysanthemum | A. Bell |
| MG (56) | V. dahliae | Indiana | Mint | A. Bell |
| PCW (124) | V. dahliae | California | Pepper | A. Bell |
| P-1-1 | V. dahliae | California | Cotton | A. Bell |
| P-1-3 | V. dahliae | California | Olive | A. Bell |
| P-1-4 | V. dahliae | Arkansas | Cotton | A. Bell |
| P-1-10 | V. dahliae | Oklahoma | Peanut | A. Bell |
| P-1-16 | V. dahliae | Illinois | Elm | A. Bell |
| P-1-19 | V. dahliae | California | Cotton | A. Bell |
| P-1-20 | V. dahliae | Texas | Cotton | A. Bell |
| P-2-1 | V. dahliae | Italy | Eggplant | A. Bell |
| P-2-2 | V. dahliae | Italy | Almond | A. Bell |
| P-2-7 | V. dahliae | Canada | Watermelon | A. Bell |
| P-2-10 | V. dahliae | Jordan | Tomato | A. Bell |
| 227 (19) | V. dahliae | Washington | Sugarbeet | A. Bell |
| BB (21) | V. dahliae | Idaho | Potato | A. Bell |
| FN (37) | V. dahliae | Australia | Flax | A. Bell |
| PS (39) | V. dahliae | Australia | Pelargonium | A. Bell |
| VW (50) | V. dahliae | Wisconsin | Velvetleaf | A. Bell |
| EN (97) | V. dahliae | The Netherlands | Eggplant | A. Bell |
| S52 | V. dahliae | Ohio | Potato | R. Rowe |
| S70 | V. dahliae | Ohio | Potato | R. Rowe |
| TO (120) | V. dahliae | Canada | Tomato | A. Bell |
| V25 | V. dahliae | Idaho | Potato | R. Rowe |
| 81-14A | V. dahliae | California | Jojoba | R. Rowe |
| 81-38A | V. dahliae | California | Guayule | R. Rowe |
| NRRL 13687 | V. dahliae | | (=CMI45492) | K. O'Donnell |
| W010 | V. dahliae | China | Cotton | K. R. Wang |
| W020 | V. dahliae | China | Cotton | K. R. Wang |
| W024 | V. dahliae | China | Cotton | K. R. Wang |
| W029 | V. dahliae | China | Cotton | K. R. Wang |
| W43 | V. dahliae | China | Cotton | K. R. Wang |
| W411 | V. dahliae | China | Cotton | K. R. Wang |
| W417 | V. dahliae | China | Cotton | K. R. Wang |
| W423 | V. dahliae | China | Cotton | K. R. Wang |
| NRRL 1204 | V. albo-atrum | | | K. O'Donnell |
| Freitag | V. albo-atrum | Wisconsin | Alfalfa | C. Grau |
| LV79 | V. albo-atrum | Wisconsin | Alfalfa | C. Grau |
| Superior | V. albo-atrum | Wisconsin | Potato | D. I. Rouse |
| DV20 | V. albo-atrum | Idaho | | J. Davis |
| Tricorpus | V. tricorpus | | | J. Davis |
| DV32 | V. tricorpus | | | J. Davis |
| DV52 | V. tricorpus | | | J. Davis |
| NRRL 13690 | V. tricorpus | | (=CMI238594) | K. O'Donnell |
| Nigrescens | V. nigrescens | | | D. I. Rouse |
| NRRL 13093 | V. chlamydosporium | | (=ATCC52033) | K. O'Donnell |
| NRRL A-3665 | V. cinnebarinum | | | K. O'Donnell |

TABLE 1-continued

Designation of identities, Geographic origins, Host Origins and Sources of Fungal Isolates

| Isolate Designation | Identification | Geographical Origins[1] | Host Origins[1] | Source[2] |
|---|---|---|---|---|
| NRRL 13900 | V. fungicola | | | K. O'Donnell |
| NRRL A-18693 | V. lateritium | | | K. O'Donnell |
| NRRL A-18240 | V. lecanii | | (=CBS297.64) | K. O'Donnell |
| NRRL A-18376 | V. psaleotae | | | K. O'Donnell |
| Fusarium sp. | Fusarium sp. | | | P. Williams |
| A149 | F. moniliforme | California | Maize | E. Smalley |
| B3852 | F. subglutinans | | Lab Cross[4] | E. Smalley |
| D4853 | F. proliferatum | | Lab Cross[5] | E. Smalley |
| F4092 | F. moniliforme | | Lab Cross[4] | E. Smalley |
| F4093 | F. moniliforme | | Lab Cross[4] | E. Smalley |
| FO1 | F. oxysporum | | | E. Smalley |
| FO23D | F. oxysporum | | | E. Smalley |
| FO119 | F. oxysporum | | | E. Smalley |
| FO916 | F. oxysporum | | Barley Grains | R. Caldwell |
| FO1042 | F. oxysporum | | Date Palms | R. Caldwell |
| FO1055 | F. oxysporum | | Carrot | R. Caldwell |
| Aspergillus | A. parasiticus | | | J. Andrews |
| Leptosphaeria | L. macubus | | | S. Leong |
| Magnaporthe | M. grisea | | Rice | A. Ellingboe |
| Neurospora | N. crassa | | | G. H. Feng |
| Sclerotinia | S. sclerotiorum | Wisconsin | Snap Beans | W. Stevenson |
| Ustilago | Ustilago maize | | | S. Leong |

Note:
[1] Blank spaces means that the origins of the isolates are not known
ATCC: American Type Culture Collection, Rockville, MD
CMI: Commonwealth Mycological Institute, Kew, England
CBS: Centraalbureau voor Schimmelcultures, Baarn, The Netherlands.
[2] J. Andrews, R. Caldwell, A. Ellingboe, C. Grau, S. Leaong, K.-N. Li, D. I. Rouse, E. Smalley, W. Stevenson, and P. Williams: Department of Plant Pathology; G. H. Feng: Department of Genetics, University of Wisconsin, Madison; A. Bell: Department of Plant Pathology, Texas A & M University; K. O'Donnell: Midwest Area National Center for Agricultural Utilization Research, USDA/ARS, Peoria, IL; R. Rowe: Department of Plant Pathology, Ohio State University, Wooster; J. Davis: Department of Plant Pathology, University of Idaho, Aberdeen.
[3] Not identified
[4] Origins described in Leslie, J. F., 1991, Mating populations in Gibberella fujikuroi (Fusarium section Liseola). Phytopathology 81:1058–1060.
[5] Personal communication J. F. Leslie: Department of Plant Pathology, Kansas State University, Manhattan.

Isolates of each of the strains in the collection were grown on potato dextrose agar at room temperature for three to seven days. Agar plugs (0.5 cm diameter) were cut from the actively growing edges of the colonies and were inoculated into two 250 ml flask containing 100 ml of potato dextrose broth. After three to seven days of incubation with constant shaking, mycelium was harvested by filtering each preparation through Whatman number 1 filter paper, rinsed with sterile distilled water, and lyophilized, and 0.2 g of the lyophilized mycelium was ground in liquid $N_2$, suspended in 4 ml of extraction buffer (50 mM Tris-Cl (pH 8.0), 850 mM NaCl, 100 mM EDTA, 1% sodium dodecyl sulfate (SDS)), and thoroughly mixed. Then 0.4 ml of 10% CTAB (Hexadecyltrimethyl-ammonium bromide) in 0.7 M NaCl was added. The mixture was then incubated at 60° C. for 15 minutes and extracted with 0.5 volume of Tris T-HCl-saturated phenyl (pH 8.0), 0.5 volume of chloroform-isoamyl alcohol (24:1) and then 1 volume of chloroform-isoamyl alcohol. The DNA was then precipitate with 2.5 volumes of 100% ethanol, rinsed with ice cold 70% ethanol, and dissolved in a 4 ml of TE buffer (10 mM Tris (pH 8.0), 1 mM ETDA (pH 8.0)) containing RNase Plus (5'–3', Inc., Boulder, Colo.). The quality of DNA was determined and the DNA concentration was determined by agarose gel electrophoresis and by spectrophotometry. All DNA extracts that were going to be used as PCR templates were diluted to a final concentration of 10 ng per µl.

Unless otherwise indicated below, all PCR reactions were performed in 25 µl (total volume) of a solution containing 0.2 mM dADP, 0.2 mM dGDP, 0.2 mM dCDP, 0.2 mM dTTP, 10 mM Tris-Cl (pH 9.0), 50 mM KCl, 2.0 mM $MgCl_2$, and 0.1% triton x-100. The resulting mixture was prepared in ice-cold stock solutions and was kept on ice until the reaction tubes were put into a pre-heated hot block kept at 95° C. The initial cycle consisted of 95° C. for 3 minutes, the annealing temperature for 1 minute, and 72° C. for 1 minute. This was followed by 34 cycles consisting of 95° C. for 1 minute, the annealing temperature for 1 minute, and 72° C. for 1 minute. The final step was a 4 minute chain extension step conducted at 72° C. The PCR was performed with a programmable DNA thermocycler. The annealing temperatures were different for different PCR primers. The PCR products were analyzed by electrophoresis and agarose gels. RAPD using the random probes listed on Table 2 below was performed on the genomic DNA of 7 V. dahliae isolates from different hosts and geographic origins, 6 isolates of V. albo-atrum and 3 isolates of V. tricorpus. Of the RAPD profile obtained, primer E20 yielded a band uniquely shared by all V. dahliae isolates and not shared by any of the other species. Southern blotting was performed and confirmed that the bands of this size from all V. dahliae isolates not only co-migrated, but also shared sequence similarity and no other band from the same samples shared any sequence homology with this particular band. The band was isolated, purified, and cloned into small pBS-KS and subsequently sequenced. Shown in FIG. 1 in this application, and presented as SEQ ID NO 1 below, is the sequence of the resulting 567 base pair DNA fragment which corresponded to this band.

Data base search has been conducted in the GenBank and other DNA libraries and no other sequence has been found homologous to this one.

TABLE 2

Code and Sequence of the RAPD Primers Tested

| Code* | Sequence 5'-3' | Code | Sequence 5'-3' |
|---|---|---|---|
| UBC502 | GCATGGTAGC | UBC559 | GAGAACTGGC |
| UBC504 | ACCGTGCGTC | UBC564 | CGGCGTTACG |
| UBC508 | CGGGGCGGAA | UBC571 | GCGCGGCACT |
| UBC515 | GGGGGCCTCA | E10 | CACCAGGTGA |
| UBC516 | AGCGCCGACG | E11 | GAGTCTCAGG |
| UBC523 | ACAGGCAGAC | E12 | TTATCGCCCC |
| UBC525 | GCTGGTTGGA | E14 | TGCGGCTGAG |
| UBC526 | AACGGGCACC | E15 | ACGCACAACC |
| UBC540 | CGGACCGCGT | E17 | CTACTGCCGT |
| UBC542 | CCCATGGCCC | E19 | ACGGCGTATG |
| UBC548 | GTACATGGGC | E20 | AACGGTGACC |
| UBC546 | CCCATGGCCC | F04 | GGTGATCAGG |
| UBC549 | CCGGCTTATG | F07 | CCGATATCCC |
| UBC550 | GTCGCCTGAG | F09 | CCAAGCTTCC |
| UBC556 | ATGGATGACG | | |

*UBC: University of British Columbia, Biotechnology Center, Canada
E and F: Operon Technologies, Inc., Almeda, California Based on the information contained in SEQ ID NO. 1, a pair of primers useful in PCR reaction were designed. The primers were designated VDS1 and VDS2, and the binding sites for the primers are designated in FIG. 1. The sequence of the primers is as follows:

VDS1 5'-ATTCAGTTCAGGAGACGGA-3'
VDS2 5'-CCGAAATACTCCAGTAGAAGG-3'

The two primers were designed based on the sequence of the two ends of the fragment. The primers were then used to attempt to amplify DNA isolated from various V. dahliae species, from other fungal isolates, the also from potato DNA. The PCR amplification results indicated that this locus is shared by all tested V. dahliae isolates from a very diversified host and geographic range of origins, but is not shared by any other fungi or plant, including the most closely related species, V. albo-atrum, V. tricorpus, and V. nigrescens, nor by any other plant wilt pathogens and microsclerotium forming organisms.

It was then decided to make a competitive internal control to be used in quantitative PCR analysis for the presence of the Verticillium dahliae. Using the V. dahliae specific primers VDSP1 and VDSP2, non-specific PCR was performed on a number of unrelated DNAs, to attempt to identify a DNA fragment which would amplify the same primers, but which would differ slightly in size from the target fragment. Such a band was then purified, cloned and sequenced. The clone fragment was from Sclerotinia sclerotiorum. That sequence is presented in SEQ ID NO 2 below. Comparison of SEQ ID NO 1 and SEQ ID NO 2 will reveal that the sequences are of unequal length and of different sequence, having in common only the two specific primers at the ends of the sequences.

Subsequently, the primers VDS1 and VDS2 were used to detect V. dahliae from a wide variety of environmental samples, and the determination of the detection limit which could be conducted for the assay in one round of PCR was tested. The limit of detection varied according to the extraction method used to extract the nucleic acids from the environmental sample, and on the number of copies of the targeted DNA present in the sample. Listed on Table 3 below is a summary of the source of DNA, the extraction method, and the detection limit which was realized.

TABLE 3

Summary of Detection Limit with Different Materials and Extraction Methods

| Source of DNA | Detection Limit | Extraction Method |
|---|---|---|
| Cloned Fragment | 50–500 copies | Liquid N2/CTAB |
| Genomic DNA | 0.1 ng DNA = 500 copies | Liquid N2/CTAB |
| Conidia | 450 conidia | Boiling/Bead Beater |
| Agar Block of Culture | 0.0006 cm$^3$ of agar block | Boiling |
| Microsclerotia in Sands | 16.5–165 microsclerotia | Liquid N2/CTAB |
| Infected Plant Tissue | 0.05 mm stem, φ 4 mm | Liquid N2/CTAB |

The results of the above Table indicate that the sensitivity of the assay is quite good. Thus, in addition to providing a very specific assay for the presence of V. dahliae, the assay is also quite sensitive and can detect the pathogen in very low quantities. In addition, the availability of the internal standard for use in competitive PCR allows the quantification of the amount of nucleic acids of the fungus found in the environmental sample.

We claim:
1. A method to assay for the presence of *Verticillium dahliae* comprising the steps of taking a sample suspected of containing *Verticillium dahliae*;

isolating nucleic acids from the sample suspected of containing *Verticillium dahliae*;

assaying the isolated nucleic acids for the presence of a DNA sequence corresponding to SEQ ID NO 1, thereby determining if *Verticillium dahliae* is present in the sample.

2. A method as claimed in claim 1 wherein the assaying of the isolated nucleic acids is conducted by polymerase chain reaction.

3. A method to assay for the presence of *Verticillium dahliae* in an agricultural field comprising the steps of taking a soil sample from the field;

testing the soil sample for the presence of a nucleic acid sequence corresponding to the SEQ ID NO 1, thereby determining if *Verticillium dahliae* is present in the soil sample.

4. A method as claimed in claim 3 wherein the assaying of isolated nucleic acids is conducted by polymerase chain reaction.

5. A method for quantitatively assaying for the presence of *Verticillium dahliae* in an agricultural field, the method comprising the steps of (a) taking a soil sample from the field;

(b) isolating nucleic acids from the soil sample;

(c) adding to the nucleic acids a known quantity of a PCR internal standard which includes sequences which are competitive in binding for PCR primers for SEQ ID NO 1, but which is different in size than the portion of SEQ ID NO 1 which lies between the binding sites for the primers on SEQ ID NO 1;

(d) performing a polymerase chain reaction (PCR) amplification of the nucleic acids using the PCR primers which will both amplify SEQ ID NO 1 and the internal standard; and (e) comparing the amount of amplified DNA produced which corresponds, in size to the internal standard to the amount of DNA produced which corresponds in size to the amplified portion of SEQ ID NO 1, thereby determining if *Verticillium dahliae* is present in the soil sample.

6. A method as claimed in claim 5 wherein the internal standard is SEQ ID NO 2.

7. A method as claimed in claim 5 wherein the comparing step is performed by electrophoretic separation of the amplified DNA followed by staining and visual comparison of band sizes produced.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 567 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Verticillium dahliae ( i x ) FEATURE:
    ( A ) NAME/KEY: primer_bind
    ( B ) LOCATION: 10..31
    ( D ) OTHER INFORMATION: /note="Binding site for PCR primer VDS1"

( i x ) FEATURE:
    ( A ) NAME/KEY: primer_bind
    ( B ) LOCATION: 149..168
    ( D ) OTHER INFORMATION: /note="Binding site of PCR Primer VDSeq1"

( i x ) FEATURE:
    ( A ) NAME/KEY: primer_bind
    ( B ) LOCATION: 406..426
    ( D ) OTHER INFORMATION: /note="Binding site of PCR Primer VDSeq2"

( i x ) FEATURE:
    ( A ) NAME/KEY: primer_bind
    ( B ) LOCATION: 510..530
    ( D ) OTHER INFORMATION: /note="Binding site of PCR Primer VDS2"

( x i ) SEQUENCE DESCRIPTION: SEQ ID NO:1:

```
AACGGTGACC ACATTCAGTT CAGGAGACGG AAGGAGGAAA TCGATCTTGA ATCTCTCGAG      60
ATCGAAGAGT GAACCCAGTT TTAGTGCGGA CTGAGCTCCA GAACTTTTTC TTGCTGGTGA     120
CATTGCACAT GGCCGGACYG TGAAGACGGG CCATCTTATC ACCTGAAGCA TAGAGTCGAT     180
ATTAGGTACA ATTTGTTCGC AAAACCGATC CGTGTTCGTG AAGAGACTCG GCCAGAGTGC     240
CTCYCACACT GGAGATAGCC TGTAACACCA CTGCTACACC ATGAAAGCCT TGTGTCATTT     300
CATGTTACCT TACCTGTCAC AAGGTCCAGT GAATGATGTT GCCACGCAAT TACTTGAGTA     360
TAGGGCCCTG GCACATGTAC CCTCRGTGTC RCGGAGGAGA CCTGCAAGTA GACCCTTCTA     420
CCCACGAATC ACACRTACTG TGAGGTTCTG TTTGCCCACC CCTCTATRAA GAAGAGACCT     480
CCCCCCTTGA GAGGGGCTCC TCTCTTGCTC CTTCTACTGG AGTATTTCGG TCCATGCATA     540
TGAAATACAT CCACTGAGGT CACCGTT                                         567
```

( 2 ) INFORMATION FOR SEQ ID NO:2:

( i ) SEQUENCE CHARACTERISTICS:
        ( A ) LENGTH: 409 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Sclerotinia sclerotiorum ( i x ) FEATURE:
        ( A ) NAME/KEY: primer_bind
        ( B ) LOCATION: 1..20
        ( D ) OTHER INFORMATION: /note="Binding site of PCR Primer VDS1"

( i x ) FEATURE:
        ( A ) NAME/KEY: primer_bind
        ( B ) LOCATION: 389..409
        ( D ) OTHER INFORMATION: /note="Binding site of PCR Primer VDS2"

( x i ) SEQUENCE DESCRIPTION: SEQ ID NO:2:

```
ATTCAGTTCA GGAGACGGAG CAAATTTTAT CAGATTCTAC TTGGGCTCCT TCAAGTAAGA      60
TCCATTCATT CGTCCTGATT CGTGGAAGCA TCCCACTCTT CTCCCAGTCA CCCTACTCTT     120
TCAAACCCGT GCCACAGGTT CATCATTCTA CCGAAACAAA TTATGAAGCT TTTAAGAAGC     180
```

| | | | | | |
|---|---|---|---|---|---|
|ATTTTGATAA|TGTAACTGAT|CGTTACGGGG|CCGTTCAAGT|GGCTTCGTTA|GTGGAGAAAC 240|
|ATGGACCTGA|GGCAATAGTT|GGTGGAGAAT|ACGAGAAGTT|GTCGACTCTT|CTCAATGTGT 300|
|CCCGAGCTGG|CGAAAACAAA|AAGCTCCATT|GGGTTTGAGT|GGTTTGATTT|CCATGCTATA 360|
|TGTAAAGGCA|TGAAATTCGA|GAACGTCACC|TTCTACTGGA|GTATTTCGG| 409|

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCATGGTAGC                    10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACCGTGCGTC                    10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGGGGCGGAA                    10

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGGGGCCTCA                    10

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AGCGCCGACG 10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACAGGCAGAC 10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCTGGTTGGA 10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AACGGGCACC 10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGGACCGCGT 10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCCATGGCCC 10

(2) INFORMATION FOR SEQ ID NO:13:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GTACATGGGC    10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCCATGGCCC    10

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCGGCTTATG    10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GTCGCCTGAG    10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

ATGGATGACG    10

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single -continued ( D ) TOPOLOGY: linear ( i i ) MOLECULE TYPE: DNA (genomic)

( x i ) SEQUENCE DESCRIPTION: SEQ ID NO:18:

GAGAACTGGC                                                10

( 2 ) INFORMATION FOR SEQ ID NO:19:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:19:

CGGCGTTACG                                                10

( 2 ) INFORMATION FOR SEQ ID NO:20:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:20:

GCGCGGCACT                                                10

( 2 ) INFORMATION FOR SEQ ID NO:21:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:21:

CACCAGGTGA                                                10

( 2 ) INFORMATION FOR SEQ ID NO:22:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:22:

GAGTCTCAGG                                                10

( 2 ) INFORMATION FOR SEQ ID NO:23:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:23:

TTATCGCCCC                                                                                      10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TGCGGCTGAG                                                                                      10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

ACGCACAACC                                                                                      10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTACTGCCGT                                                                                      10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ACGGCGTATG                                                                                      10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AACGGTGACC                                                                                      10

(2) INFORMATION FOR SEQ ID NO:29:

( i ) SEQUENCE CHARACTERISTICS:
   ( A ) LENGTH: 10 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:29:

GGTGATCAGG 10

( 2 ) INFORMATION FOR SEQ ID NO:30:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:30:

CCGATATCCC 10

( 2 ) INFORMATION FOR SEQ ID NO:31:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:31:

CCAAGCTTCC 10

( 2 ) INFORMATION FOR SEQ ID NO:32:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:32:

ATTCAGTTCAGGAGACGGA 19

( 2 ) INFORMATION FOR SEQ ID NO:33:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:33:

CCGAAATACTCCAGTAGAAGG 21